United States Patent [19]
Borland et al.

[11] Patent Number: 5,068,430
[45] Date of Patent: Nov. 26, 1991

[54] BLEACHING OF COLORED AMINE OXIDES

[75] Inventors: James E. Borland; Y.-D. Mark Chen; Joe D. Sauer; Kim R. Smith; Rebecca F. Smith, all of Baton Rouge, La.

[73] Assignee: Ethyl Corporation, Richmond, Va.

[21] Appl. No.: 558,094

[22] Filed: Jul. 26, 1990

[51] Int. Cl.$^5$ .............................................. C07C 291/00
[52] U.S. Cl. .................................... 564/298; 564/297; 204/157.82
[58] Field of Search ............... 564/298, 297, 299, 497, 564/498, 499; 204/157.63, 157.82, 157.83,

[56] References Cited

FOREIGN PATENT DOCUMENTS

| | | |
|---|---|---|
| 2106415 | 8/1972 | Fed. Rep. of Germany . |
| 0273703 | 7/1988 | German Democratic Rep. . |
| 0999343 | 7/1965 | United Kingdom . |

*Primary Examiner*—Allen J. Robinson
*Assistant Examiner*—Brian M. Burn
*Attorney, Agent, or Firm*—Patricia J. Hogan

[57] ABSTRACT

Amine oxides, such as amine oxide dihydrates, which have become discolored by being prepared from tert-amines and hydrogen peroxide in a liquid medium constituting not more than 50% of the weight of the reaction mixture and in the presence of carbon dioxide are bleached by exposing them to visible light, preferably incandescent light having a luminosity of at least about 1750 lumens.

9 Claims, No Drawings

BLEACHING OF COLORED AMINE OXIDES

FIELD OF INVENTION

This invention relates to amine oxides and more particularly to a process for bleaching amine oxides which have become discolored by being prepared in the presence of carbon dioxide.

BACKGROUND

Amine oxides are materials which have been found to have a variety of applications and have been used, e.g., in the treatment of fabrics and in the preparation of hair conditioners and shampoos, toothpaste, laundry detergent powders, fabric softeners, and toilet soap bars, as well as in other applications.

When synthesized in the conventional manner so as to be provided as dilute solutions, the amine oxides have acceptable color, even when they are prepared in the presence of carbon dioxide, as in U.S. Pat. No. 4,247,480 (Murata et al.). This is not the case, however, when the amine oxides are prepared by the newer high solids processes, such as the processes of copending application Ser. No. 415,910 (Smith et al.), filed Oct. 2, 1989. When amine oxides are prepared by the reaction of amines with hydrogen peroxide in a medium which constitutes not more than 50% of the weight of the reaction mixture, they have acceptable color when the reaction is conducted in the absence of carbon dioxide; but they are intensely colored when carbon dioxide is used to speed the reaction.

SUMMARY OF INVENTION

It has now been found that amine oxides having acceptable color can be obtained by exposing a carbon dioxide-discolored amine oxide to visible light until the amine oxide is bleached.

DETAILED DESCRIPTION

The amine oxides which are bleached in accordance with the present invention are amine oxides which have become discolored by being prepared in the presence of carbon dioxide. Since this discoloration occurs only when a high solids process is used, they are products obtained by reacting a tert-amine with hydrogen peroxide in the presence of carbon dioxide in an amount of liquid medium that constitutes not more than 50% of the weight of the reaction mixture.

The amines which are used in such processes are well known and include a variety of tert-amines having aliphatic, cycloaliphatic, and/or aromatic groups attached to the amino nitrogen. However, they are generally trialkylamines corresponding to the formula $RR'R''N$ wherein R, R', and R'' are primary alkyl groups containing 1-30 carbons, preferably such trialkylamines in which R is methyl or ethyl, R' is an alkyl group containing 6-20 carbons, and R'' is independently selected from methyl, ethyl, and alkyl groups containing 6-20 carbons.

Exemplary of the tert-amines that may be used are trimethylamine, triethylamine, N-isobutyldimethylamine, trihexylamine, N,N-dimethyl-2-ethylhexylamine, N-eicosyldimethylamine, N-isobutyl-N-triacontylmethylamine, N-benzyldimethylamine, N-ethyldibenzylamine, N,N-diisobutyl-4-t-butylbenzylamine, tri-2-hydroxyethylamine, and, more preferably, the N-alkyldimethyl- and N,N-dialkylmethylamines in which the alkyl groups are hexyl, octyl, decyl, dodecyl, tetradecyl, hexadecyl, octadecyl, and/or eicosyl, as well as mixtures of such amines.

In the high solids processes, the hydrogen peroxide that is reacted with the tert-amine is generally an aqueous hydrogen peroxide having a concentration of 50-99%, preferably 50-70%; and the amount employed is at least the stoichiometric amount but usually not more than a 20% molar excess.

The reaction is conducted in a medium which comprises an organic solvent and the water contributed by the aqueous hydrogen peroxide. Organic solvents that may be used are preferably solvents in which the tert-amine and amine oxide are soluble at the reaction temperatures but in which the amine oxide is insoluble at a lower temperature, so that the product can be precipitated from the reaction mixture as a dehydrate, as in Smith et al., the teachings of which are incorporated herein in toto by reference.

The organic solvent is preferably a substantially inert ester, hydrocarbon, halohydrocarbon, or highly polar aprotic solvent; and it is preferably used only in the amount required to maintain a stirrable reaction mixture. Exemplary of such solvents are ethyl, butyl, or sec-butyl acetate, methyl propionate, methyl benzoate, toluene, heptane, N,N-dimethylformamide, and N,N-dimethylacetamide.

The amine oxide synthesis is conducted by adding the aqueous hydrogen peroxide to the amine, preferably at a controlled rate, in the presence of carbon dioxide and preferably also in the presence of a chelating agent, such as diethylenetriaminepentacetic acid or ethylenediaminetetraacetic acid, at a temperature of about 20°-100° C., preferably 60°-80° C., a temperature which is maintained for 1-24 hours before the reaction mixture is cooled. The organic solvent may be present initially but is generally just added dropwise as needed to maintain a stirrable reaction mixture.

When, as in Smith et al., it is desired to prepare an amine oxide dehydrate, the concentration and amount of aqueous hydrogen peroxide are selected so as to provide a water/amine oxide mol ratio of about 2/1, or the water content of the reaction mixture is adjusted by the addition or removal of water before recovering the product so as to achieve that ratio. The product so prepared is an amine oxide dehydrate or a mixture thereof with anhydrous amine oxide and/or amine oxide monohydrate.

As prepared in these high solids processes, the amine oxides are intensely colored, and they are exposed to visible light in accordance with the present invention until they are bleached to a lighter color or to white. This light exposure can be made before the amine oxides are recovered from their reaction mixtures when the carbon dioxide is no longer present, or it can be made after the amine oxides have been recovered.

The visible light employed is preferably light having a luminosity of at least about 1750 lumens and is preferably incandescent light. The time required for the bleaching varies with various factors, such as the degree of bleaching desired, the degree of luminosity of the light source, and the distance of the light source from the amine oxide being bleached; but it is easily determined by routine experimentation. When the light source is a 100-watt incandescent light bulb, it has been found that exposure of an organic solvent slurry of bright orange N-tetradecyldimethylamine oxide dehydrate to the light for four hours bleaches the oxide to a pale yellow-white.

What is claimed is:

1. A process which comprises exposing a carbon dioxide-discolored amine oxide to visible light until the amine oxide is bleached.

2. The process of claim wherein the light has a luminosity of at least about 1750 lumens.

3. The process of claim 2 wherein the light is incandescent light.

4. The process of claim 1 wherein the discolored amine oxide is a product obtained by reacting a tert-amine with hydrogen peroxide in the presence of carbon dioxide in an amount of liquid medium that constitutes not more than 50% of the weight of the reaction mixture.

5. The process of claim 4 wherein the tert-amine is a compound corresponding to the formula RR'R''N in which R, R', an R'' are primary alkyl groups containing 1-30 carbons.

6. The process of claim 5 wherein R is methyl or ethyl, R' is an alkyl group containing 6-20 carbons, and R'' is independently selected from methyl, ethyl, and alkyl groups containing 6-20 carbons.

7. The process of claim 4 wherein the medium comprises an organic solvent in which the tert-amine and amine oxide are soluble at the reaction temperatures but in which the amine oxide is insoluble at a lower temperature.

8. The process of claim 4 wherein the amine oxide is exposed to the visible light in the absence of carbon dioxide before being recovered from the reaction mixture.

9. The process of claim 4 wherein the amine oxide is exposed to the visible light after being recovered from the reaction mixture.

* * * * *

UNITED STATES PATENT AND TRADEMARK OFFICE
CERTIFICATE OF CORRECTION

PATENT NO. : 5,068,430

DATED : November 26, 1991

INVENTOR(S) : James E. Borland et al.

It is certified that error appears in the above-identified patent and that said Letters Patent is hereby corrected as shown below:

Column 3, line 7, reads "claim" and should read -- claim 1 --.

Signed and Sealed this

Sixteenth Day of March, 1993

*Attest:*

STEPHEN G. KUNIN

*Attesting Officer*   Acting Commissioner of Patents and Trademarks